(12) United States Patent
Clarke et al.

(10) Patent No.: US 8,123,509 B2
(45) Date of Patent: Feb. 28, 2012

(54) INJECTION MOLDING PROCESS FOR THE PREPARATION OF AN ORAL DELIVERY DEVICE FOR THE PHARMACEUTICALLY ACTIVE AGENT

(75) Inventors: Allan J. Clarke, Collegeville, PA (US); Robert Glinecke, Collegeville, PA (US); Ronald Raby, King of Prussia, PA (US); Chi Leung Li, Harlow (GB); Luigi Martini, Harlow (GB)

(73) Assignee: SmithKline Beecham Limited, Brentford, Middlesex (GB)

( * ) Notice: Subject to any disclaimer, the term of this patent is extended or adjusted under 35 U.S.C. 154(b) by 0 days.

(21) Appl. No.: 12/627,330

(22) Filed: Nov. 30, 2009

(65) Prior Publication Data

US 2010/0221292 A1    Sep. 2, 2010

Related U.S. Application Data

(62) Division of application No. 10/487,853, filed as application No. PCT/EP02/09274 on Aug. 20, 2002, now Pat. No. 7,638,081.

(30) Foreign Application Priority Data

Aug. 28, 2001 (GB) .................................. 0120835.4

(51) Int. Cl.
*B29C 45/14* (2006.01)
(52) U.S. Cl. ...................... 425/116; 425/125; 425/129.1
(58) Field of Classification Search .................. 425/125, 425/110, 116, 123–124, 129.1
See application file for complete search history.

(56) References Cited

U.S. PATENT DOCUMENTS 1,734,727 A    11/1929    Herold
(Continued)

FOREIGN PATENT DOCUMENTS

EP    1057478    12/2000
(Continued)

*Primary Examiner* — Richard Crispino
*Assistant Examiner* — Thukhanh Nguyen
(74) *Attorney, Agent, or Firm* — Dara L. Dinner; Theodore Furman

(57) ABSTRACT

An injection molding process for the preparation of an oral delivery device comprising a core which contains a pharmaceutically active agent, having a coating with one or more openings leading to such a core. The invention also relates to devices produced by the process, and to injection molds suitable for performing the process.

2 Claims, 3 Drawing Sheets

U.S. PATENT DOCUMENTS

| | | | |
|---|---|---|---|
| 2,965,589 A | 12/1960 | Price | |
| 4,076,791 A | 2/1978 | Barter et al. | |
| 4,470,786 A * | 9/1984 | Sano et al. | 425/125 |
| 5,004,614 A | 4/1991 | Staniforth | |
| 5,071,607 A | 12/1991 | Ayer et al. | |
| 5,213,808 A | 5/1993 | Bar-Shalom et al. | |
| 5,580,578 A | 12/1996 | Oshlack et al. | |
| 5,681,584 A | 10/1997 | Savastano et al. | |
| 5,997,793 A | 12/1999 | Lahnala | |
| 6,096,339 A | 8/2000 | Ayer et al. | |
| 6,180,129 B1 | 1/2001 | Eckenhoff et al. | |
| 6,183,466 B1 | 2/2001 | Ferrari et al. | |
| 7,384,451 B2 | 6/2008 | Shiraishi et al. | 95/19 |
| 2005/0109211 A1 | 5/2005 | Shiraishi et al. | 95/241 |

FOREIGN PATENT DOCUMENTS

| | | |
|---|---|---|
| JP | A-04-341813 | 5/1991 |
| JP | A-05-131492 | 5/1993 |
| JP | A-06-344358 | 6/1993 |
| JP | A-08-008363 | 1/1996 |
| JP | A-08-039606 | 2/1996 |
| JP | A-08-192446 | 7/1996 |
| JP | A-11-207749 | 8/1999 |
| JP | A-11-333882 | 12/1999 |
| JP | A-01-156025 | 6/2001 |
| WO | WO89/09066 | 10/1989 |
| WO | WO99/18159 | 4/1999 |
| WO | WO03/068195 | 8/2003 |

* cited by examiner

INJECTION MOLDING PROCESS FOR THE PREPARATION OF AN ORAL DELIVERY DEVICE FOR THE PHARMACEUTICALLY ACTIVE AGENT

This application is a divisional application of U.S. application Ser. No. 10/487,853 filed 4 Aug. 2004 now U.S. Pat. No. 7,638,081, (allowed) which is a §371 of international application No. PCT/EP2002/09274 filed 20 Aug. 2002, and which claims priority of GB Application No. 0120835.4 filed 28 Aug. 2001.

The present invention relates to a novel process for the preparation of an oral delivery device for a pharmaceutically active agent. In particular, the invention relates to a process for the preparation of an oral delivery device comprising a core which contains the active agent, having a coating with one or more openings leading to such a core. The invention also relates to novel oral delivery devices obtainable by the process of this invention.

The coating of tablet cores comprising an active agent, for example to prepare a pharmaceutical tablet for oral administration, is well established practice. The common reasons for so doing include: improved product mechanical integrity; improved stability to the surrounding environment (particularly air, moisture and light); a means of modifying the release rate of the active agent; and in order to achieve distinctive or improved aesthetic characteristics. Processes for coating are also well established in the art.

Of the factors described above, the use of a coating to control the rate of release of an active agent has received considerable attention and, indeed, many different devices have been developed for such a purpose. Some of the devices utilised are discussed in U.S. Pat. No. 5,004,614. This patent describes a controlled release device with an impermeable coating having an orifice for release of drug when the device has been orally administered and is immersed in an aqueous medium such as gastro-intestinal fluid. Such devices are prepared either according to pressure coating or dip coating methods and the orifice is formed by removing sections of the formed coating with laser or mechanical drilling techniques.

It is an object of this invention to provide an alternative process for the preparation of devices of the above described type. It is a particular object of this invention to provide an improved process for the manufacture of devices of the type disclosed in U.S. Pat. No. 5,004,614, the contents of which are incorporated herein by reference. It is also an object of the invention to provide novel constructions of devices of this general type. Other objects and advantages of the invention will become apparent from the following description.

The present invention therefore provides, in a first aspect, a process for the preparation of a delivery device comprising a core which includes a pharmaceutically active agent covered by an outer coating which includes one or more openings communicating from the exterior of the device to the core characterised in that the outer coating is applied by injection moulding said coating around said core.

A process for making a device according to this invention may, for example, comprise the steps of:

providing, if necessary preparing, the core of the device comprising a pharmaceutically active agent;

locating said core within a mould cavity surrounding the core, said mould cavity defining the required dimensions of the outer coating and preferably also defining the required position, shape and dimensions of the one or more openings;

injecting a fluid mouldable material into said mould cavity;

allowing the material to set to thereby form the outer coating;

separating the formed device from the mould cavity.

The core may be prepared by compressing suitable ingredients for the core to form a compacted mass which comprises the core of the device (also referred to herein as "tablet core"). This may be prepared using conventional tablet excipients and formulation compression methods. Thus, the core would typically comprise the active agent or agents along with excipients that impart satisfactory processing and compression characteristics such as diluents, binders and lubricants. Additional excipients that may form part of the core of the device include disintegrants, flavourants, colorants and release modifying agents. Typically the active agent and excipients are thoroughly mixed prior to compression into a solid core. The core of the device can be formed by conventional tablet-forming processes such as wet granulation methods, dry granulation methods or by direct compression. The core can be produced according to any desired pre-selected shape such as bi-convex, hemi-spherical, near hemi-spherical, round, oval, generally ellipsoidal, oblong, generally cylindrical or polyhedral, e.g. a triangular prism shape.

A preferred shape of core is one which is generally of cylindrical shape having two opposite facing generally convex circular end faces. Such convex end faces may be of a generally part-spherical domed convex shape, or generally conical or frustro conical. Another preferred shape of core is a convex or of a bi-convex shape comprising two opposite-facing domed surfaces which are generally circular or elliptical in plan.

The term "near hemi-spherical" is intended to be construed in the manner described in U.S. Pat. No. 5,004,614. The term "cylindrical" is intended to include both true cylindrical shapes and distorted cylindrical shapes. Preferably the core is formulated into a bi-convex shape, e.g. having two domed opposite surfaces. If the core has corners, e.g. corners between cylindrical side surfaces and convex end surfaces, a rounded corner radius of ca. 1 mm is preferred to assist flow of the fluid coating material during injection.

The core could be produced in a multi-layered (e.g. bi- or tri-layered) form.

The delivery device of the invention is most suitable as an oral delivery device, as it can conveniently be made in the shape and size of a pharmaceutical tablet, well known to those acquainted with pharmaceutical technology. The core can comprise active agents which are suitable for use in a wide range of therapies, particularly for oral delivery, and include those listed U.S. Pat. No. 5,004,614. The quantity of active agent present within the core is a matter to be determined based upon typical pharmaceutical considerations, e.g. known dosages for the active materials contained therein, and is not limited by the process of this invention or the structure of the delivery devices formed thereby.

It will be appreciated that to carry out the process of this invention, the tablet core must be accurately located within the mould cavity to thereby achieve a precisely defined thickness of coating and/or positioning of the one or more opening. Preferably the tablet core is located via robotic means.

The core of the device is coated with a suitable material by an injection moulding process. Injection moulding generally involves the injection of a molten thermoplastic, fluid-like material, often a fluid polymer under pressure and usually at an elevated temperature, into a precisely made die cavity in a mould block. Upon cooling, typically to ambient temperature, the fluid material solidifies to form a solid product reproducing the internal shape of the cavity. Alternatively the injection moulding process may use a thermosetting fluid-like material, for example injecting the material in a fluid state into a heated mould, where the heat acts upon the thermosetting material to solidify it. Silicone materials are known thermosetting materials. Such moulding techniques are well known in the art of manufacture of small plastic material components. Typical injection moulding apparatus comprise a polymer feed system, consisting of a polymer reservoir, e.g. a hopper of polymer pellets or granules, a heater and a screw pump that forces the fluid polymer down an injection port towards the mould.

The injection moulding process of this invention can be carried out on a standard injection moulder, e.g. of a hot or cold runner type. A hot runner system is preferred, and although valve gates could be used to eliminate the gate pip, in practice the very small residual gate pip left by conventional hot runner machines is likely to be insignificant. Such apparatus is capable of operating over a wide range of temperatures and pressures. It will be appreciated however, that a principal factor affecting the utility of this invention is the capability of the tablet core to withstand the rigours of injection moulding conditions. For example many pharmaceutically active agents are complex organic compounds which are susceptible to thermal degradation at elevated temperatures, which may be exacerbated by simultaneous application of high pressure. Therefore it is preferred to use temperatures for the injection moulding process which are considered to minimise or ideally avoid any thermal degradation for the active agent in question. For many such agents suitable processing conditions to achieve this are specified in the literature. For these reasons, it is believed that typical operational conditions would be between temperatures of 25-300° C., more typically 50-250° C. and especially 50-150° C. Preferably the injection moulding pressure should be less than 6000 psi (ca. 400-450 kg/cm$^2$) to avoid damage to a tablet core within the mould cavity, typically pressures of 200 to 1000 psi (ca. 14-70 kg/cm$^2$), more typically 400 to 600 psi (ca. 30-45 kg/cm$^2$) have been found suitable. Conversely the tablet core should be made of materials and using suitable conditions that the core can withstand such pressures within the mould without breaking or crumbling.

The material of the outer coating may be any material which blocks (either permanently of for a suitable time period) exposure of the core to an environmental fluid, e.g. a gastro-intestinal fluid, and is not removed by dissolution or otherwise disrupted before a predetermined duration for controlled, delayed or sustained release of the active material in the core has occurred. Alternatively, the coating material may be selected because of aesthetic considerations. Any pharmaceutically acceptable fluid mouldable material which exhibits thermoplastic properties can be used as an outer coating for the tablet core, and suitable materials include thermoplastic organic polymers. Those skilled in the art of injection moulding characterise the flow properties of polymeric materials according to a melt flow index which ranges from 1 g/10 min (very poor flow) to 50 g/10 min (very high flow). It has been found that materials that exhibit a melt flow index in the range of 15-30 g/10 min are particularly suitable for use in this invention. Representative materials and their blends suitable for use as a coating material in this invention include those listed in U.S. Pat. No. 5,004,614. Preferred coating materials include the polymethacrylate copolymers, natural waxes and lipids, and biodegradable polymers in general. Other suitable polymer materials include polyvinyl acetates, such as the 40 and 20 grades thereof, cellulose acetate, butyrate and phthalate, EVA (ethylene vinyl acetate) or HPC (hydroxypropyl cellulose), silicones, or copolymers of methacrylic acid, methylmethacrylate, and methyl acrylate, such as that known as 4135F, available from Röhm polymers, or a blend based on 4135F. 4135F comprises a methacrylic acid, methyl-methacrylate, methyl acrylate copolymer in a typical ratio 25:65:10 with a dissolution threshold of pH greater than 7.2.

Accordingly in a further aspect, the present invention provides a device adapted for oral delivery of a pharmaceutically active agent, when made by a process as described herein. Typically such a device comprises a core which includes a pharmaceutically active agent covered by an outer coating which includes one or more openings communicating from the exterior of the device to the core characterised in that the outer coating is a polymeric material exhibiting a melt flow index which ranges from 1 g/10 min (very poor flow) to 50 g/10 min (very high flow), especially that exhibits a melt flow index in the range of 15-30 g/10 min, applied by injection moulding said coating around said core.

The thickness of the outer coating can be readily adapted. For devices such as those described in U.S. Pat. No. 5,004,614 it is important that, for materials that do exhibit a certain degree of permeability to environmental fluids, that the coating is applied at such a thickness to prevent exposure to the core before the desired duration of the controlled release has passed. For immediate release devices a considerably thinner coating could be utilised or a coating applied which is designed to dissolve in gastro-intestinal fluid. It is believed that a suitable coating thickness that can be achieved by this process of this invention is the range of 0.1 mm to 2 mm, preferably in the range 0.2 to 0.8 mm, more preferably in the range 0.1 to 0.6 mm Typically tablet cores may be made with a tolerance of ±0.025 mm on a cylindrical diameter, and ±0.1 mm on a cylindrical height. Typically there might be variation of less than 0.03 mm in an injection mould cavity, and these figures indicate typical tolerance ranges for the thickness of the coating achievable by the process of this invention. An important factor to consider is the melt flow index of the thermoplastic polymer. Thus, to obtain the thinnest coating section it will be necessary to use a polymer with a high melt flow characteristics. Even small thickness variations can have significant effects on melt flow, and as a coating thickness of nominally 0.6-0.4 mm appears to be optimum from the point of view of the moulding process, although pharmaceutical requirements of the delivery device might require other thicknesses.

A mould suitable for use in the process of this invention has a cavity in which the tablet core may be located with a space around the said core to define the required shape and dimensions of the coating, with one or more internal member extending from the interior surface of the mould cavity to abut the said core and to define the shape and position of the said one or more opening. Typically the mould will incorporate plural cavities to maximise the production rate of the process, as is standard practice in the injection moulding art. Typically the mould might include 16 cavities. The internal members define the openings of the device. Such internal members are preferably designed without any overhang between them and the interior surface of the mould cavity, so that they can be easily separated from the device produced therein without any damage occurring to the coating. These internal members may also serve to hold the core in place as the fluid coating material is injected into the mould cavity.

In a preferred construction of mould, one or more internal member is resiliently mounted, e.g. spring-mounted, so as to be able to move reciprocally resiliently inward and outward relative to the mould cavity. By this construction such a resilient internal member can apply a resilient pressure to a core when enclosed in the mould cavity to help to hold the core in place within the mould cavity. Also the ability of such a member to move slightly when it contacts a tablet core on closing the mould can help to relieve any pressures on the core which might tend to break the core, and can help the internal member to accommodate to variations in the size between tablet cores. Preferably the resilient mounting of such an internal member should be such as to apply a resilient pressure of up to 200 psi (ca. 14 kg/cm$^2$) to the tablet core, or conversely to be resiliently moveable under such a pressure applied thereto.

It is also preferred to provide an internal member with a vacuum conduit passing therethrough to the outside of the mould, by which reduced pressure may be applied to a tablet core in contact with the member to assist in retaining the core in place in the mould. Suitably the vacuum conduit may pass through a resiliently mounted internal member as described above. Such a vacuum conduit may be useful both in moulds which close along a horizontal axis such that the reduced pressure prevents the cores from falling out of the cavity, and also moulds which close along a vertical axis so that the reduced pressure supplements gravity in holding the core in place.

Normally an injection mould has one fixed part and a second moving part which moves into contact with the fixed part to close the mould. Suitably the resilient member and any vacuum conduit could be on this fixed part.

For use with a mould as described above having an internal member it is preferred to provide the core with at least one small seating indentation of a shape generally corresponding to the part of the member that contacts the core, and so positioned on the core that when the mould encloses a tablet core, the member seats in the indentation. This can help to positively locate the core in the mould cavity and to secure the core in place in the mould cavity. In the above-described bi-convex core such an indentation may be located on one or both of the convex surfaces, e.g. the convex end surfaces of the generally cylindrical core. Such an indentation may be need to be at most 1.5 mm deep, and preferably for example may need to be only ca. 0.005 cm deep. Suitably such an indentation is tapered to be narrowest at its bottom, e.g. having a frustro-conical profile. The core may also be provided with one or more, preferably at least three small seating projections e.g. ribs, to engage with the inner surface of the mould cavity, e.g. with corresponding concavities therein, to assist in locating the core within the mould cavity. Such projections may be shaped to make only a point contact with the mould cavity so as to avoid resulting in the formation of any corresponding opening through the coating.

Generally the mould cavity is made in a multi-part, preferably a two part mould construction, which close together with great precision, where each part defines a respective part of the mould cavity. When assembled together the two mould parts define an internal cavity i.e. such that, on closure, a cavity around the tablet core is defined which corresponds to the required dimensions of the coating. Such a construction further allows the mould cavity to be opened to allow the formed device to be separated from the mould. Moulds of this general type for use in injection moulding processes are well known in the art. The one or more internal members can be located at any suitable position on the inner wall surface of the mould cavity and are preferably made integral with the mould. Where a multi-part construction is utilised the internal members may be located upon one or more mould parts. The parts of such a multi-part mould may close horizontally, i.e. along a horizontal axis, or vertically, i.e. along a vertical axis. A horizontally closing mould is preferred.

The mould may also incorporate one or more pairs of retractable side cores which can move together to grip a tablet core when the core has been located in a part of the mould, to help to hold the core in place until the mould is fully closed. Such side cores may be particularly useful in a horizontally closing mould.

A typical process of the invention may involve the steps (1) loading tablet cores into a feeder, e.g. a vibratory bowl feeder, for discharge onto one or more conveyor, from which the tablet cores can be collected in the alignment required for picking up by a robot equipped with suction grippers, (2) the robot placing the tablet cores onto a register station to accurately position them in the spatial arrangement required for insertion into the mould cavities, (3) a robot picking up the tablet cores and inserting them into the mould cavities, (4) performing the injection of coating material, (5) if a vertically closing mould is used, removing the completed devices from the mould cavities using a robot. Step (2) might be eliminated, e.g. by designing a collection device at the end of the conveyor with sufficient accuracy that subsequent alignment on a register is not required. Steps (3) and (4) might be combined by designing a robot with two sets of grippers, one to hold the tablet cores and one to hold the completed articles, so whilst the mould is open the gripper head could extract the completed devices, index sideways, and place new tablet cores into the cavities.

The invention also provides, in a further aspect, a die or mould suitable for use in the moulding process, which has a cavity in which a tablet core may be located and being of dimensions such as to leave a space around the said core to define the required shape and dimensions of the coating, with one or more internal members extending from the interior surface of the mould cavity to abut the said core.

It will be appreciated that the required shape, size, number of openings and the geometric arrangement of openings required for the device can be readily achieved by a suitable arrangement of the shape, size, number and relative positions of the internal members(s) on the mould or mould part. Any single opening can be as fine as 0.1 um and up to as large as a face of the tablet core e.g. 10 mm. Typical openings would be in the range 0.5 mm-4 mm. Preferably, the opening(s) of the device will comprise about 10-60% of the total face area of the device. The opening may have any convenient shape, but is preferably rounded, e.g. substantially circular or elliptical.

For example, in one embodiment the device may comprise a core which is generally of cylindrical shape having two opposite facing substantially circular end faces or of a bi-convex shape comprising two opposite-facing domed surfaces which are generally circular or elliptical in plan, covered with an outer coating which generally conforms to the outer shape of the core, the coating having two opposite facing openings therein communicating with substantially the centre of each of said respectively substantially circular or domed surfaces.

The injection moulding process of this invention can be used to produce a device which can be used for immediate, delayed or sustained release, for example to achieve release of the active agent at a pre-determined part of the gastro-intestinal tract. Those skilled in the art, when considering the release profile of a device containing an active agent, would consider factors such as drug solubility, the surface area and number of openings, coating thickness and the tablet core formulation properties. It will be appreciated that such variations in device can be readily accommodated by the process of this invention.

This process differs from known methods inter alia in that the coating is applied to create the device in a single operation i.e. no further processing of the coating is required such as mechanical drilling of the coat to expose the core. It permits an improved method of producing devices with a varying number, size and shape of openings. Moreover, the accuracy of opening size is more reproducible. It is believed that this process is more robust and simpler to operate than known methods and is particularly suitable for mass production of such devices.

The invention will now be described by way of example only with reference to the accompanying drawings.

FIGS. 1 to 3 schematically shows sequential stages in the use of the process to make a device in accordance with this invention.

Figure 1:
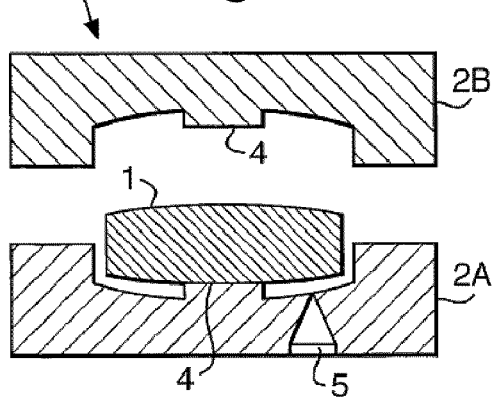
Figure 2:
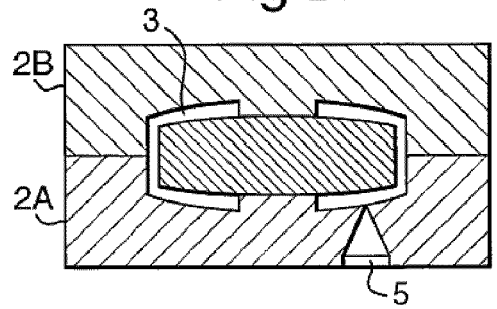
Figure 3:
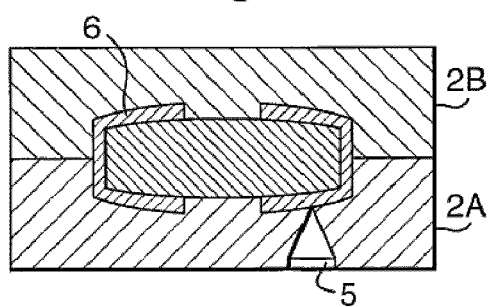

With respect to FIGS. 1 to 3, a tablet core 1 is shown within a mould overall 2, made in two mating halves 2A and 2B. The core 1 is of a generally cylindrical shape having two opposite facing substantially circular end faces and cylindrical side walls, and FIG. 1 shows this cylindrical core in longitudinal section. The mould defines a cavity 3 which defines the shape of the coating to be applied to the tablet core, each of the two halves 2A and 2B defines a part cavity so that when the two halves 2A and 2B are put together the entire cavity 3 is defined. The cavity 3 conforms closely to the shape and dimensions of the core 1, but leaves a gap around the core 1 which subsequently defines the thickness of the coating to be formed therein.

Extending from the inner wall of the mould cavity 3 are internal members being projections 4 integrally formed with the mould parts 2A and 2B. These projections 4 abut against the core 1 when this is within the mould cavity 3, and serve both to hold the core in place within the cavity, preventing the core from being dislodged when coating material is injected into the cavity, and to define the size, shape and position of the openings to be formed in the coating. These projections 4 are shaped without any overhang between them and the inner wall of the mould cavity, to allow the projections to be removed from the subsequently formed coating without damaging the coating. Suitably the projections 4 may taper, being narrowest at the end remote from the inner wall of the mould cavity.

In FIG. 1 the mould 2 is shown in an open configuration, with a fixed mould part 2A lowermost, and the tablet core 1 resting on the projection. In FIG. 2 the mould 2 has been closed, so that the projection 4 of the upper mould part 2B has come into contact with tablet core 1.

In FIG. 3 a molten coating material 6 has been injected into the cavity 3 via injection port 5 positioned at a convenient point on the fixed part 2A of the mould 2. Following cooling the two mould parts 2A and 2B are opened and the formed device 7 is ejected.

Figure 4:
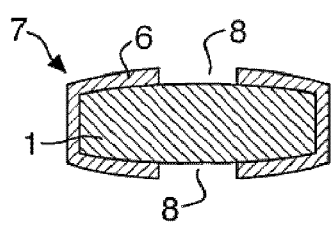
FIGS. 4 and 5 show a device as made using the process of this invention.
Figure 5:
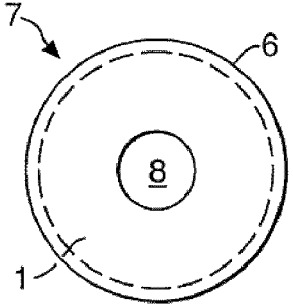

The device 7 is shown in cross section and a plan view respectively in FIGS. 4 and 5, and comprises the core 1, enclosed by the coating 6, through which extend the two openings 8 corresponding to the respective positions of the two projections 4.

Figure 6:
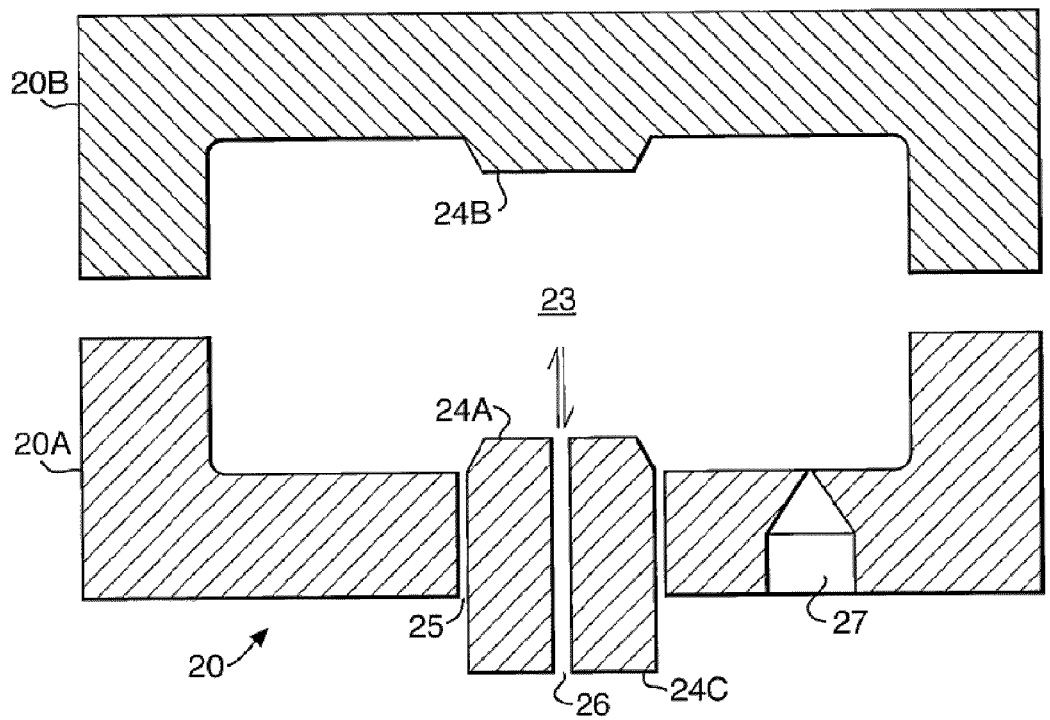
FIG. 6 shows a preferred injection mould for the process of the invention.
Figure 8:
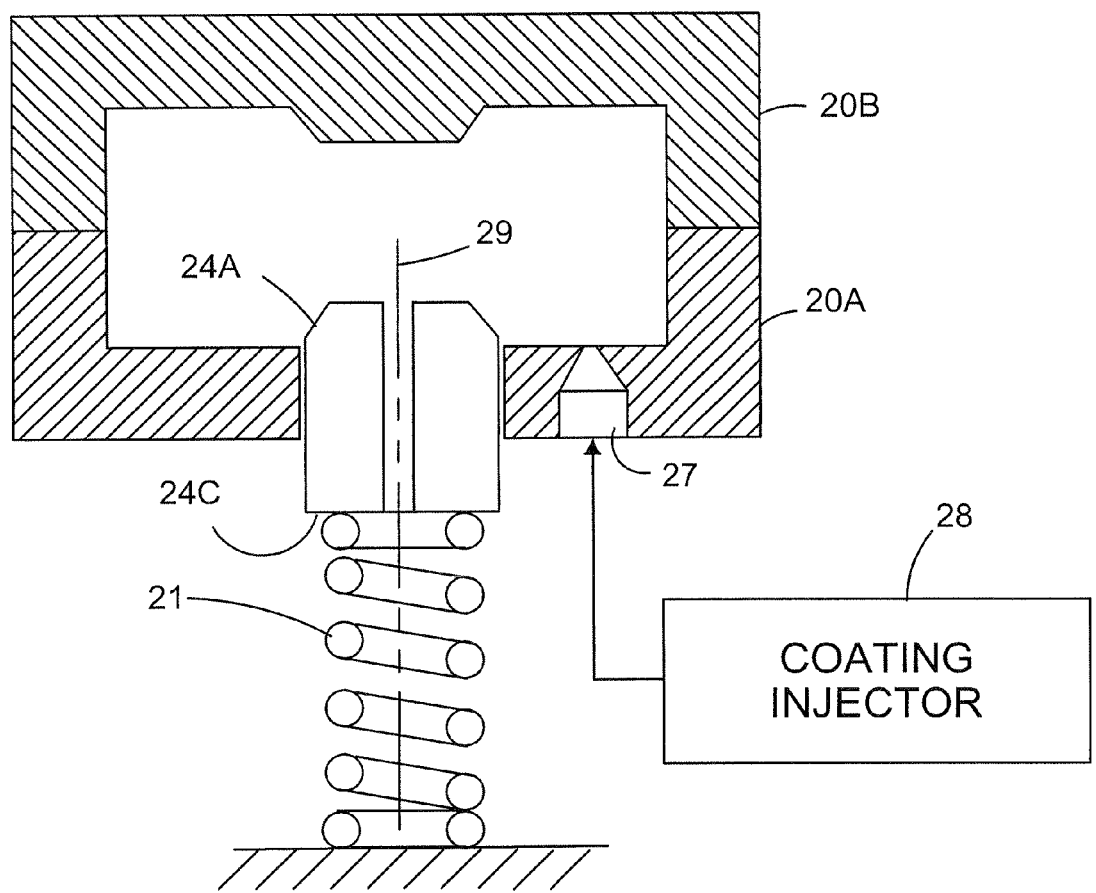
FIG. 8 shows the injection mold in a closed condition with a projection-biasing spring and a coating injector.

In FIG. 6 a preferred construction of mould 20 is shown in cross section. This has two parts 20A, 20B corresponding to those 2A, 2B of mould 2. These parts 2A, 2B have internal projections 24A, 24B corresponding to those 4 of mould 2. Each projection 24A, 24B is of a frusto conical shape, widest at its base where it meets the inner surface of the mould cavity 23. The projection 24A in the fixed part 20A is resiliently reciprocally moveable in the direction of the arrows in FIG. 6 (along an imaginary line 29 in FIG. 8), under the biasing action of a spring 21 (FIG. 8) bearing upon its end 24C outside the mould part 20A, and the projection 24A is slideably mounted in a guide channel 25 passing through the mould part 20A (the clearance in the channel 25 between the part 24A and the mould part 20A is exaggerated for clarity). The resilient mounting of the projection 24A is such as to move under a downward pressure of ca. 200 psi from a tablet core (not shown) bearing thereon. Passing through projection 24A 10 is a vacuum conduit 26, via which a partial vacuum can be applied to such a tablet core resting on projection 24A downwards. There is an injection gate 27 in the lower fixed mould part 20A for injection of fluid coating material under pressure by a coating injector 28 (FIG. 8). In order to form the openings through the outer coating of the tablet being produced, the projection 24A must remain in contact with the core during injection of the fluid coating material. Accordingly the biasing force exerted by the spring 21 must be sufficient to prevent the pressure of the fluid coating material within the mold cavity from moving projection 24A out of engagement with the core during the injection of the fluid coating material through gate 21.

Figure 7:
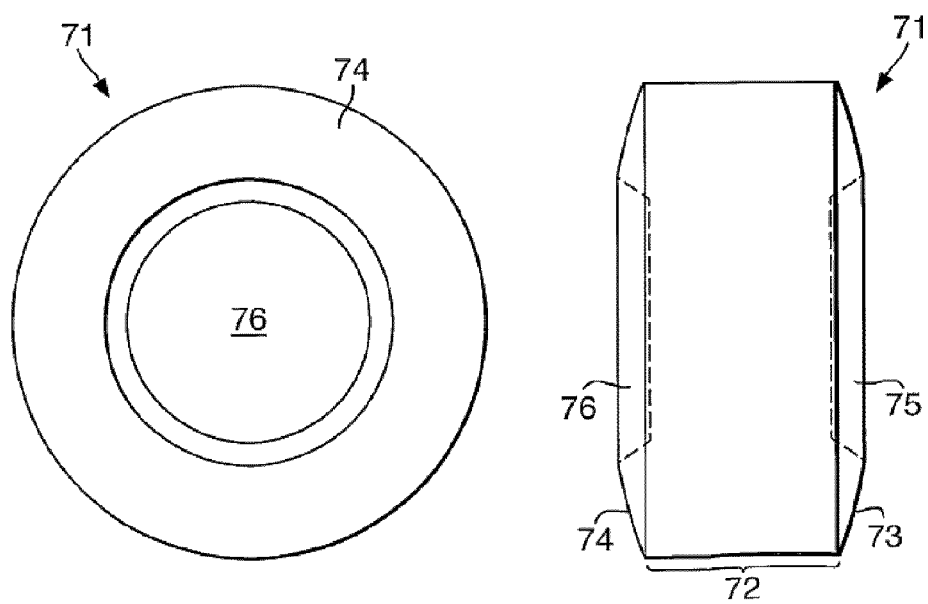
FIG. 7 shows a preferred shape of tablet core.

Referring to FIG. 7 a preferred tablet core shape 71 is shown in plan (FIG. 7A) and in side view (FIG. 7B). The shape is generally cylindrical, with a cylindrical part 72 having spherically domed convex end faces 73, 74. In each face 73, 74 is an indentation 75, 76 of a profile each matching the convex frustro-conical profile of the projections 24A, 24B of the mould 20. The slope of the conical sides of these indentations is ca 35° relative to the longitudinal cylindrical axis of the core 71. The diameter of the outer rim of each indentation 75, 76 is ca. 70-75% of the overall diameter of the cylindrical shape, and the depth in the longitudinal direction is ca. 0.4 mm.

EXAMPLE 1

The following tablet cores were formed by conventional means by mixing together the active ingredients with excipients and compressing to form the tablet core. These examples are intended to be by way of illustration rather than limitation.

Tablet core a) represents a core that is suitable for use in an immediate release formulation which consists of 10% active ingredient, 60% microcrystalline cellulose, 24% lactose, 5% starch glycolate (disintegrant) and 1% magnesium stearate (lubricant).

Tablet b) represents a core that is suitable for use in a controlled release formulation which consists of 10% active ingredient, 40% hydroxypropylmethyl cellulose (HPMC), 24% lactose, 20% microcrystalline cellulose, 5% starch glycolate and 1% magnesium stearate.

The coating material used was a low density polyethylene produced by Exxon Chemical. The grade was LD600BA natural. This material demonstrates a wide range of processing temperatures (160 to 240° C.) and has a melt flow index of 20.5 g/10 min. Operating conditions utilised were 150° C. and pressure of 400 psi.

The injection moulding machine used was a 35T Arburg.

The tablet cores shown in FIGS. 1 to 5 and 7 typically had a diameter of 8 mm. The coating had a thickness, as defined by the gap in the cavity between the core and the inner wall of the cavity of ca. 0.5 mm. The openings 7 in the coating were typically circular in shape having a diameter of 1 mm, or ca. 6 mm using the core shape shown in FIG. 7.

It has been found that these injection moulding operating conditions did not have an adverse effect on the tablet core i.e. mechanical integrity was maintained.

The invention claimed is:

1. A mold for forming a device comprising a core which includes a pharmaceutically active agent covered by an injection-molded outer coating having at least one opening communicating from the exterior of the device to the core, in which the outer coating is applied by injection molding of said coating around said core, said mold having a cavity in which said core may be located with a space around the said core to define the required shape and dimensions of the coating and a guide channel leading from the mold cavity to the exterior of the mold, said mold cavity having an interior surface, at least one internal member extending from the interior surface of the mold cavity, and mounted for sliding movement relative to the mold cavity in said guide channel in both directions along an imaginary line extending through said core, to abut the said core and to define the shape and position of the said at least one opening, means for injecting a moldable fluid into said space around said core to form said outer coating, and resilient means bearing on a portion of said at least one internal member located outside the mold and urging said at least one internal member into abutment with the core with a biasing force sufficient to prevent pressure exerted by the injected moldable fluid on said at least one internal member from moving said at least one internal member out of engagement with the core.

2. A mold according to claim 1, having two parts which are separable from each other, and which come together by relative vertical movement.

* * * * *